US010895506B1

(12) United States Patent
Lander et al.

(10) Patent No.: US 10,895,506 B1
(45) Date of Patent: Jan. 19, 2021

(54) METHOD AND DEVICE FOR MEASURING SUBJECT'S BODY TEMPERATURE

(71) Applicant: Innotech International LLC, Wilmington, DE (US)

(72) Inventors: Victor Lander, Short Hills, NJ (US); Jacob Gitman, Bay Harbor Island, FL (US)

(73) Assignee: INNOTECH INTERNATIONAL, LLC, Wilmington, DE (US)

( * ) Notice: Subject to any disclaimer, the term of this patent is extended or adjusted under 35 U.S.C. 154(b) by 0 days.

(21) Appl. No.: 16/926,282

(22) Filed: Jul. 10, 2020

(51) Int. Cl.
*A61B 1/06* (2006.01)
*G01J 5/04* (2006.01)
*G01J 5/08* (2006.01)
*G01J 5/00* (2006.01)

(52) U.S. Cl.
CPC .............. *G01J 5/0025* (2013.01); *G01J 5/047* (2013.01); *G01J 5/089* (2013.01); *G01J 5/0896* (2013.01); *A61B 1/0692* (2013.01)

(58) Field of Classification Search
CPC .......... G01J 5/0025; G01J 5/047; G01J 5/089; G01J 5/0896; A61B 1/0692
See application file for complete search history.

(56) References Cited

U.S. PATENT DOCUMENTS

| | | | | |
|---|---|---|---|---|
| 1,453,006 | A * | 4/1923 | Day | A61B 1/0692 600/248 |
| 1,632,851 | A * | 6/1927 | Reaves | A61B 3/0008 600/248 |
| 4,494,881 | A * | 1/1985 | Everest | G01J 5/08 250/353 |
| 6,377,400 | B1 * | 4/2002 | Hollander | G01J 5/02 359/618 |
| 6,614,830 | B1 * | 9/2003 | Hollander | G01J 5/08 359/618 |
| 9,536,355 | B1 * | 1/2017 | Kumar | G01J 5/00 |
| 2009/0161348 | A1 * | 6/2009 | Spartano | F21V 29/70 362/105 |
| 2020/0061651 | A1 * | 2/2020 | Cordani | A62C 31/03 |

* cited by examiner

*Primary Examiner* — Randy W Gibson
(74) *Attorney, Agent, or Firm* — Henry M. Fiereisen LLC

(57) ABSTRACT

A hands-free measuring by an operator a temperature of a subject is carried out by arranging a remote temperature measuring module including a contactless infrared thermometer with a laser providing a pointer spot, on an operator's head, positioning the operator with the applied temperature measuring module at a safe distance from the subject, moving the operator's body and/or head so as to point the contactless infrared thermometer and the laser pointer spot at the subject hands-free, activating the temperature measuring module and thereby measuring a temperature of the subject by the contactless infrared thermometer hands-free, and displaying the measured temperature of the subject on a digital display.

12 Claims, 5 Drawing Sheets

METHOD AND DEVICE FOR MEASURING SUBJECT'S BODY TEMPERATURE

FIELD OF THE INVENTION

The present invention relates to methods and devices for remote measurements of temperature of human subjects with the use of an infrared thermometer directed to a subject, such as for example on his forehead, and thus allowing to obtain temperature readings in real time.

DESCRIPTION OF PRIOR ART

It is known that beside traditional thermometers, such as mercury thermometers with temperature readings obtained by contacts with the patient, infrared thermometers have been presently used in the medical equipment industry, which are capable of detecting the temperature of a given subject based on generated infrared emission. These thermometers operate using a sensor that detects the infrared radiation emitted from a body region of a subject, whose temperature measurements are to be carried out.

A particular type of the infrared thermometers is a so-called "non-invasive thermometer" with which the sensor is maintained at a distance (i.e. without a material contact) from a surface of the subject whose thermal level is desired to be determined. The thermometers of this type are hold by hand of an operator and have to be positioned at a near proximity, typically 1 cm to 5 cm, from a detection surface of a patient in order to receive infrared emissions coming from a predetermined area of the patient with high selectivity.

The task of remotely screening of employees, patients, airport passengers, people in customs control points becomes especially important considering current Covid19 virus global epidemic. Society for Human Resource Management (SHRM) issued specific recommendations in their website (https://www.shrm.org/resourcesandtools/legal-and-compliance/employment-law/pages/eeoc-coronavirus-temperature.aspx) as "A Guide to Employee Temperature Checks", in which 6 feet recommended as a minimum safe distance.

However currently with the use of the known thermometers employees, passengers, and other people undertaking temperature screening procedures will not be able to keep recommended 6 ft (1.8 m) distance from an operator who must measure the temperature, because the operator must use his hands to hold the thermometer and work in close proximity to the subject. Therefore, the person administering the procedure as well as the subject take serious risk to be infected, because the standard use of hand-held infrared thermometer requires a temperature to be taken at a few centimeters distance from the subjects' forehead.

While the above described known technique enables reliable measurements of the patient's temperature to be obtained, it however has some operating drawbacks. This type of measurements forces an operator to position himself much closer to the subject than is currently recommended and even required-"social distance" of 6 feet (1.8 m). As a result, this increases a possibility of a mutual infection for personal administering the procedure as well as for people subjected to the temperature measurement screening.

SUMMARY OF THE INVENTION

Accordingly it is an object of the present invention to eliminate the above-specified disadvantages of the prior art, in particular by providing a method of and a device for measuring a temperature of a subject, which allow temperature measurement by an operator utilizing a non-invasive thermometer and positioned at a distance of at least 6 feet from a subject and without a direct contact with the latter, so as to minimize or even completely avoid a risk of infection of the operator by the subject and vice versa.

In keeping with these objects and with others which will become apparent hereinafter, one feature of the present invention resides, briefly stated, in a method of hand-free measuring by an operator a temperature of a subject, which comprises arranging a remote temperature measuring module including a contactless infrared thermometer with a laser providing a pointer spot, on an operator's head, positioning the operator with the applied remote temperature measuring module at a safe distance from the subject, moving the operator so as to point the contactless infrared thermometer and the laser pointer spot at the subject hands-free, activating the remote temperature measuring module and thereby measuring a temperature of the subject by the contactless infrared thermometer hands-free, and displaying the measured temperature of the subject on a digital display.

Another feature of the present invention resides in a device for hands-free measuring by an operator a temperature of a subject, which comprises a remote temperature measuring module including a contactless infrared thermometer with a laser providing a pointer spot, a digital display, means for arranging the remote temperature measuring module including the contactless infrared thermometer with the laser providing the pointer spot on the operator's head so that the operator with the applied remote temperature measuring module is located at a safe distance from the subject, and means for activating the remote temperature measuring module and thereby measuring a temperature of the subject by the contactless infrared thermometer such that when the operator is moved so that the contactless infrared thermometer and the laser pointer spot point at the forehead of the subject and, a temperature of the subject is measured by the contactless infrared thermometer and the measured temperature of the subject is displayed on the digital display hands-free.

When the method is implemented and the device is designed and operated according to the present invention as specified hereinabove, measurements by an operator of a subject's temperature can be executed with the operator positioned at a safe distance of at least 6 feet or more from the subject and without a direct contact with the subject, so as to minimize or even completely avoid a risk of infection of the operator by the subject and vice versa.

According to a further feature of the present invention the measuring a temperature of the subject by the contactless infrared thermometer includes detecting with the contactless infrared thermometer an intensity of an infrared radiation coming from a target area which is a forehead of the subject, which intensity of the infrared radiation coming from the forehead of the subject is indicative of a blood heat of the subject and thereby the temperature of the subject.

According to still a further feature of the present invention the activating of the remote temperature measuring module is carried out by pressing at least one button on the remote temperature measuring module.

According to still a further feature of the present invention after the activating of the remote temperature measuring module, the measuring of the temperature of the subject with the contactless infrared thermometer by detecting with the contactless infrared thermometer the intensity of the infrared radiation starts automatically.

According to still a further feature of the present invention the moving of the operator so that the contactless infrared thermometer and the laser pointer spot point at the subject includes carrying out movements of the operator by moving an operator's body, or by moving an operator's head, or by moving both an operator's head and an operator's body.

According to still a further feature of the present invention the arranging of the remote temperature measuring module including the contactless infrared thermometer with the laser providing the pointer spot on the operator's head includes applying a transparent protective face shield on an operator's face, and arranging the remote temperature measuring module including the contactless infrared thermometer with the laser providing the pointer spot, on the transparent protective face shield.

According to still a further feature of the present invention the arranging of the remote temperature measuring module including the contactless infrared thermometer with the laser providing the pointer spot on the operator's head includes attaching a head band to remote the temperature measuring module, and mounting the remote temperature measuring module including the contactless infrared thermometer with the laser providing the pointer spot on the operator' head using the attached head band.

Further features and advantages of the present invention will be best understood from the detailed description of preferred, but not exclusive, embodiments of the present invention, which is accompanied by the following drawings.

DETAILED DESCRIPTION OF THE PREFERRED EMBODIMENTS

Figure 1:
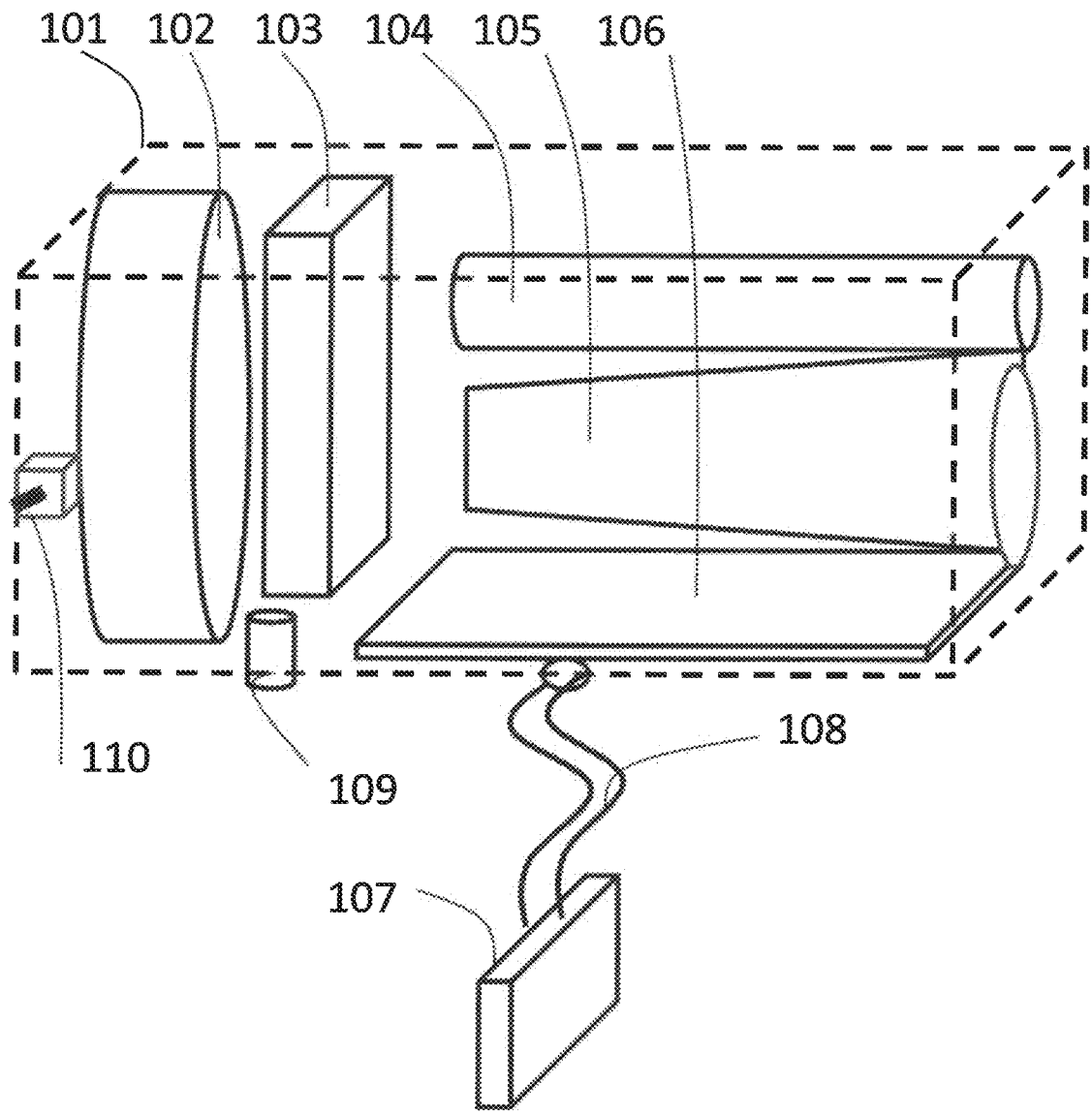
FIG. 1 of the drawings is a view showing a block-diagram of a device for hand-free measuring by an operator a temperature of a subject according to the present invention, with a remote temperature measuring module including its major blocks.

A device for hand-free measuring by an operator a temperature of a subject according to the present invention has a remote temperature measuring module which is schematically shown in FIG. 1 of the drawings. It has a housing 101, a battery 102, a power supply unit 103, and a contactless infrared thermometer. The contactless infrared thermometer has a laser pointer 104 providing a pointer spot, an infrared sensor 105, a PC board with a microprocessor 106, and a digital display 107 connected with the microprocessor 106 by wires extending through a semi-rigid conduit 108. The temperature measuring module further has a coaxial socket 109 for a connection to a charger, and a power on/off switch 110 for activating/deactivating.

Infrared radiation from the field of view on a subject is received by the infrared sensor 105 with an optical structure corresponding to D/S value between 72 and 36. The low power laser pointer 104 is used for correct aiming of the field of view on the subject. The current generated by the infrared sensor 105 is directed to the PC board 106 with the microprocessor with corresponding electronics. The module is powered by the battery 102 with the power conditioning unit 103. DC current corresponding to the intensity of the infrared radiation from a subject is transformed to digital signals by the microprocessor 106 and transmitted by the wires inside of these mi-rigid conduit 107 to the digital display 108.

Figure 2:
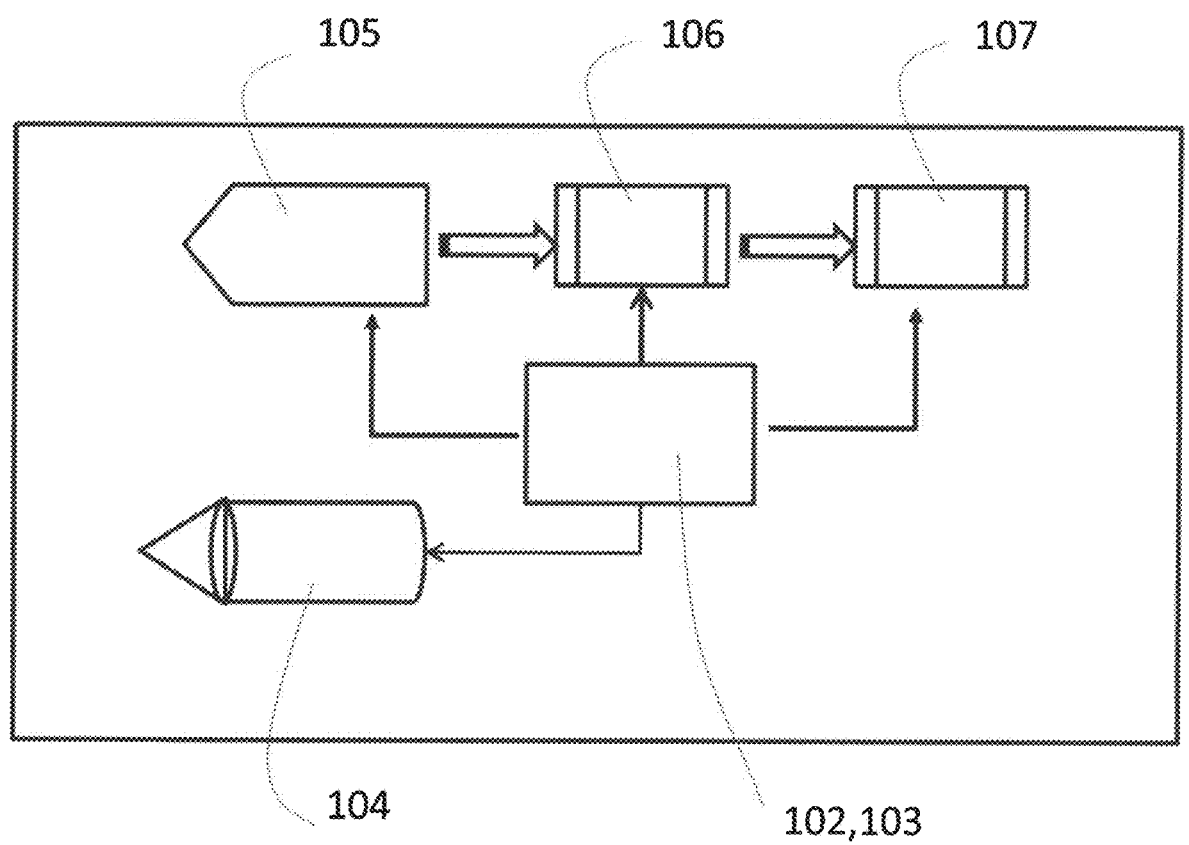
FIG. 2 of the drawings is a view showing a schematic diagram of the remote temperature measuring module of the device for hand-free measuring by an operator a temperature of a subject according to the present invention, with interconnections between its major blocks.

FIG. 2 shows interconnections inside the remote temperature measuring module and between components of the device. The infrared sensor 105, low power laser pointer 104, the digital display 108 are powered from the rechargeable power supply unit 103 with the rechargeable battery 102, and the power on/off switch 110. DC current proportional to infrared power intensity from a target (a subject) 301 and generated by the infrared sensor 105 is digitized by the microprocessor 106 and transmitted to the display 107 via the wires run through the semi-rigid conduit 108.

Figure 3:
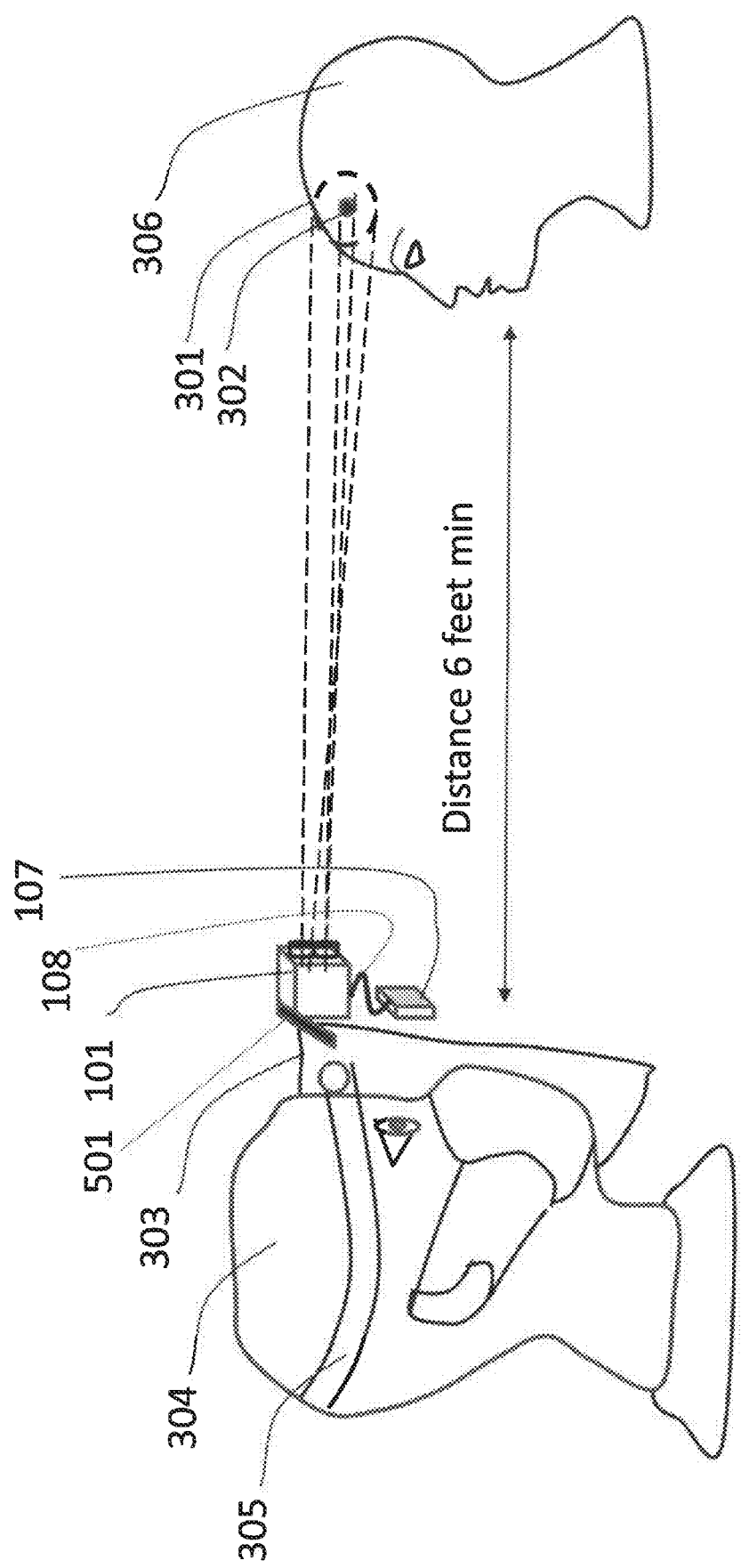
FIG. 3 of the drawings shows a temperature measurement with the remote temperature measuring module of the device for hand-free measuring by an operator a temperature of a subject, which is mounted on a protective face shield of the operator using a spring clip, and a position of a target spot and a measurement area on a forehead of the subject, according to the present invention.

FIG. 3 show the remote temperature measurement module which is arranged on a transparent protective face shield 303, by its housing 101 mounted on the latter. The infrared sensor 105 and low power laser pointer 104 are assembled in the module in such way that horizontal axes of these components are parallel and a pointing spot 302 from the laser pointer is located approximately at a center of a measurement area 301 of the infrared sensor. The measurement area 301 over a typical human subject forehead of a is approximately 1" to 2" in diameter. In order to allow a remote operation with a distance between the operator 304 and the subject 305 of at least 6 feet, the infrared sensor 105 must have a technical parameter distance to spot ratio D/S between 72 and 36, which is currently widely available.

As shown in FIG. 3, an operator 304 positions himself at a safe distance of at least 6 feet from the subject. The operator turns on the remote temperature measuring module and mounts it on the face shield 303 that is held on an operator's head 304 for example by an adjustable band 305 in such a way that the display 107 is visible to the operator without obstructing the observation of the subject by adjusting the semi-rigid conduit 108. When the power is turned on, the low power laser pointer 104 will produce a small visible red spot of an approximate diameter of 0.25". By small movements of his head and/or body the operator 304 positions the pointer spot of low power laser pointer 104 at the center of the forehead of the subject and takes a reading of the temperature from the display 107. The digital display 107 is calibrated in such a way that beside showing a measured temperature, a background light of the digital display 107 changes its color from green to red if the measured temperature is above 98.6 F (37 C), which indicated that the subject has a fever. The operator observes the measured temperature and color of the display and takes appropriate action.

Figure 4:
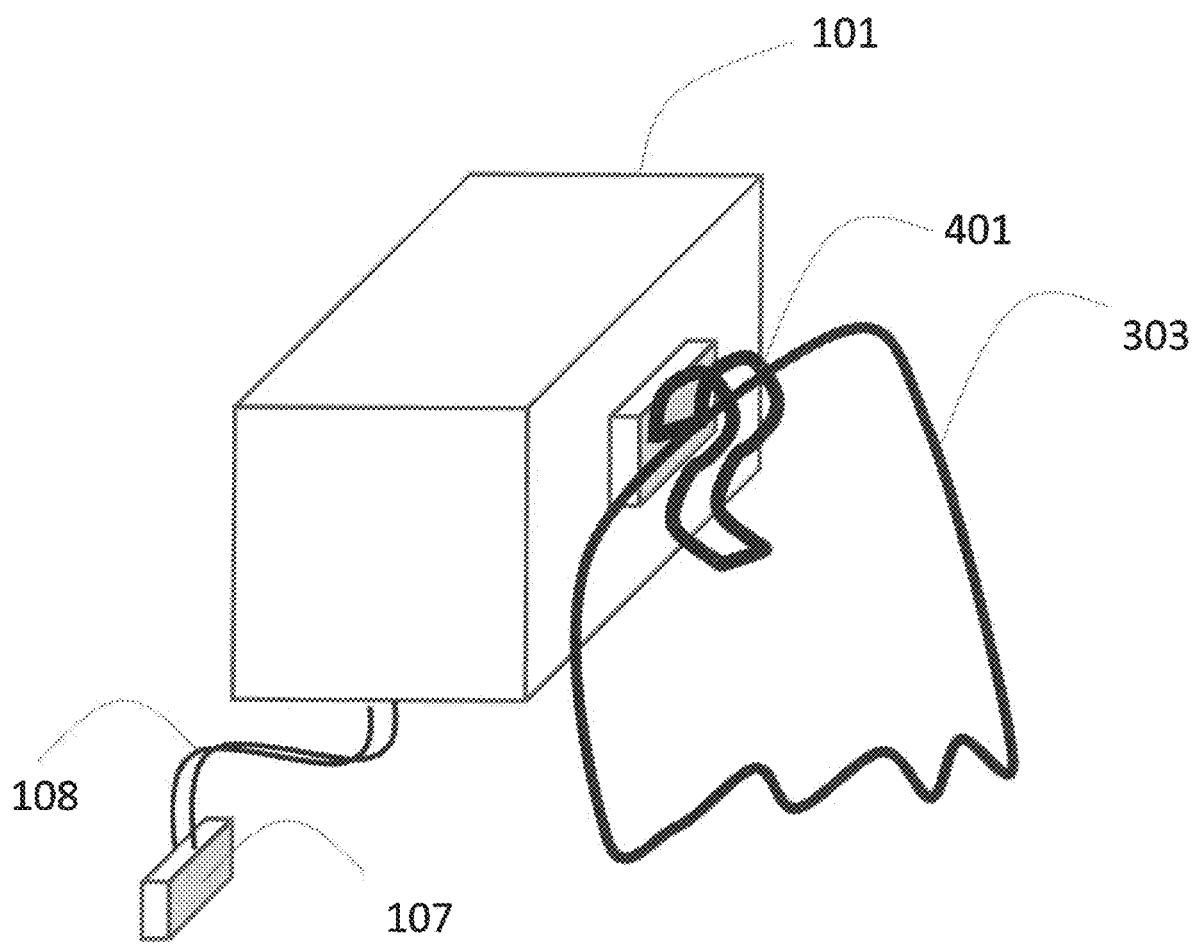
FIG. 4 of the drawings shows details of a removable spring mounting on the face shield of the module of the device for hand-free measuring by an operator a temperature of a subject, according to the present invention.

FIG. 4 shows details of a spring-loaded face shield mounting mechanism for the remote temperature measuring module. The face shield 303 slides under a spring 401 and the remote temperature measuring module is held on the face shield 303 by a pressure force of the spring 401. The face shield 303 is squeezed between the body of the remote temperature measuring module 101 and the spring 401 and remains safely in place during the temperature measuring process. Attachment of the spring 401 to the remote temperature measuring module housing 101 and assembly of the remote temperature measuring module can be performed by any known assembly methods such as using screws, epoxy glue, stamping, etc. The spring 401 itself can be composed of metal wire or plastic materials. This construction allows easy dismantling the remote temperature measuring module from the shield for cleaning and maintenance.

Figure 5:
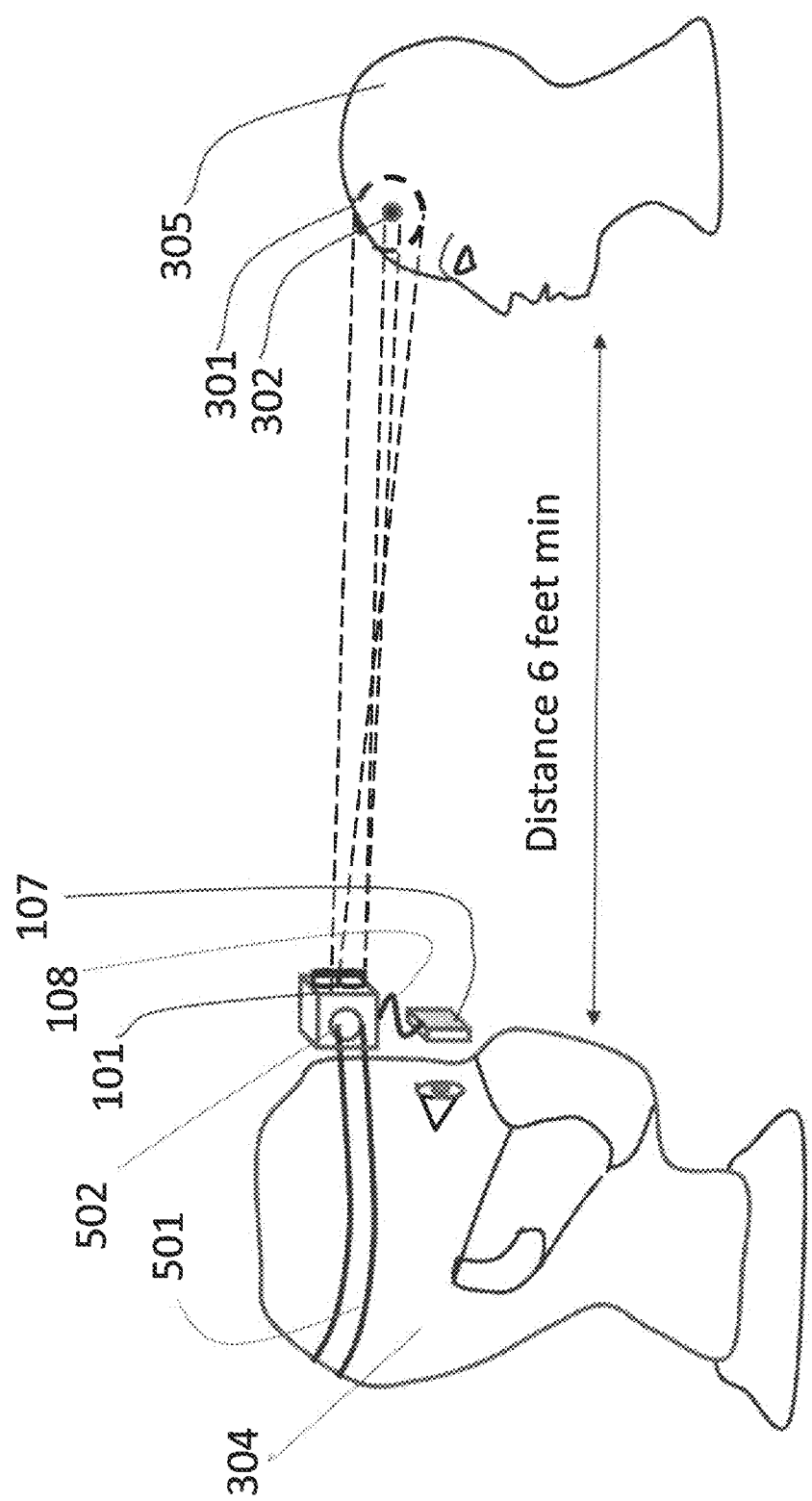
FIG. 5 of the drawings shows the module of the device for hand-free measuring by an operator a temperature of a subject, mounted on the forehead of the operator using a headband, according to the present invention.

FIG. 5 shows another embodiment of the present invention, in which the operator does not use a protective face shield but instead wears a soft face mask covering operator's nose and mouth. In this case the remote temperature measuring module 101 can be attached to the operator's head using a head band 501 which can be similar to the one used for the face shield attachment. For this purpose, the housing 101 of the remote temperature measuring module can use a standard band attachment element 502, which may include a screw, a button plug in, or any other typical head-band attachment mechanism. A temperature measurement procedure is similar to the temperature measurement procedure of the remote temperature measuring module provided with the face shield mounting mechanism.

The present invention is not limited to the embodiments specified hereinabove and their details shown, and it can be implemented with other embodiments which are different from them but realized within the scope of the invention.

What is desired to be protected by Letters Patent is set forth in particular in the appended claims.

We claim:

1. A method of hand-free measuring by an operator a temperature of a subject, comprising
    arranging a remote temperature measuring module including a contactless infrared thermometer with a laser providing a pointer spot, on an operator's head;
    positioning the operator with the applied remote temperature measuring module at a safe distance from the subject;
    moving the operators body and/or head so as to point the contactless infrared thermometer and the laser pointer spot at the subject hands-free;
    activating the remote temperature measuring module and thereby measuring a temperature of the subject by the contactless infrared thermometer hands-free;
    displaying the measured temperature of the subject on a digital display;
    transforming by a microprocessor of the contactless infrared thermometer a DC current corresponding to an intensity of infrared radiation from the subject to digital symbols and transmitting them by wires inside a semi-rigid conduit to the digital display which is connected with the microprocessor by the wires extending inside the semi-rigid conduit; and
    mounting the remote measuring module on a face shield that is held on an operator's head so that the display is visible to the operator without obstructing observation of the subject.

2. A method of hand-free measuring by an operator a temperature of a subject of claim 1, wherein the process of measuring a temperature of the subject by the contactless infrared thermometer includes detecting with the contactless infrared thermometer an intensity of an infrared radiation coming from a target area which is a forehead of the subject, which intensity of the infrared radiation coming from the forehead of the subject is indicative of a blood heat of the subject and thereby the temperature of the subject.

3. A method of hands-free measuring by an operator a temperature of a subject of claim 1, wherein the activating of the remote temperature measuring module is carried out by pressing at least one button on the remote temperature measuring module.

4. A method of hands-free measuring by an operator a temperature of a subject of claim 1, wherein after the activating of the remote temperature measuring module, the measuring of the temperature of the subject with the contactless infrared thermometer by detecting with the contactless infrared thermometer the intensity of the infrared radiation starts automatically.

5. A method of hands-free measuring by an operator a temperature of a subject of claim 1, wherein the process of pointing the contactless infrared thermometer and the laser providing the pointer spot at the forehead of a subject includes carrying out movements of the operator by moving an operator's body, or by moving an operator's head, or by moving both an operator's head and an operator's body.

6. A method of hands-free measuring by an operator a temperature of a subject of claim 1, wherein the mounting the remote measuring module on a face shield includes the mounting the remote measuring module on a transparent protective face shield.

7. A device for hand-free measuring by an operator a temperature of a subject, comprising
    a remote temperature measuring module including a contactless infrared thermometer with a laser providing a pointer spot;
    a digital display;
    means for arranging the remote temperature measuring module including the contactless infrared thermometer with the laser pointer on the operator's head so that the operator with the applied remote temperature measuring module is positioned at a safe distance from the subject;
    means for activating the remote temperature measuring module and thereby measuring a temperature of the subject by the contactless infrared thermometer such that when the operator is moved so that the contactless infrared thermometer and the laser pointer spot points hands-free at the subject and the remote temperature measuring module is activated, a temperature of the subject is measured by the contactless infrared thermometer and the measured temperature of the subject is displayed on the digital display hands-free,
    wherein the contactless infrared thermometer has a microprocessor transforming a DC current corresponding to an intensity of infrared radiation from the subject to digital symbols and transmitting them by wires inside a semi-rigid conduit to the digital display which is connected with the microprocessor by the wires extending inside the semi-rigid conduit wherein the remote measuring module is mounted on a face shield which is held on an operator's head so that the display is visible to the operator without obstructing observation of the subject.

8. A device for hands-free measuring by an operator a temperature of a subject of claim 7, wherein the remote temperature measuring module including the contactless infrared thermometer with the laser providing the pointer spot is designed so that a measuring a temperature of the subject by the contactless infrared thermometer includes detecting with the contactless infrared thermometer an intensity of an infrared radiation coming from a target area which is a forehead of the subject, which intensity of the infrared radiation coming from the forehead of the subject is indicative of a blood heat of the subject and thereby the temperature of the subject.

9. A device for hand-free measuring by an operator a temperature of a subject of claim 7, wherein the means for activating of the remote temperature measuring module include at least one button provided on the remote temperature measuring module and pressable by the operator.

10. A device for hand-free measuring by an operator a temperature of a subject of claim 7, wherein the remote temperature measuring module including the contactless infrared thermometer with the laser providing the pointer spot at the subject is designed so that after the activating the remote temperature measuring module, the measuring a temperature of the subject with the contactless infrared thermometer carried out by detecting with the contactless infrared thermometer an intensity of an infrared radiation starts automatically.

11. A device for hand-free measuring by an operator a temperature of a subject of claim 7, wherein the means for arranging the remote temperature measuring module including the contactless infrared thermometer with the laser providing the pointer spot on an operator's head are formed so that the moving the operator so that the contactless infrared thermometer and the laser pointer spot point at the subject can be provided by carrying out movements of the operator by moving an operator's body, or by moving an operator's head, or by moving both an operator's head and an operator's body.

12. A device for hands-free measuring by an operator a temperature of a subject of claim 7, wherein the face shield is a transparent protective face shield.

* * * * *